United States Patent [19]

Egawa et al.

[11] Patent Number: 5,449,472
[45] Date of Patent: Sep. 12, 1995

[54] LUBRICATING OIL FOR COMPRESSION-TYPE REFRIGERATORS

[75] Inventors: Tatsuya Egawa; Yasuhiro Kawaguchi; Kenji Mogami; Nobuaki Shimizu, all of Sodegaura, Japan

[73] Assignee: Idemitsu Kosan Co., Ltd., Tokyo, Japan

[21] Appl. No.: 66,240

[22] Filed: May 25, 1993

[30] Foreign Application Priority Data

Jun. 4, 1992 [JP] Japan .................................. 4-143922
Sep. 7, 1992 [JP] Japan .................................. 4-237842

[51] Int. Cl.$^6$ ...................... C09K 5/04; C10M 105/18
[52] U.S. Cl. ................................ 252/68; 252/52 A; 252/67
[58] Field of Search ............... 252/68, 67, 52 R, 52 A; 526/332, 333, 334

[56] References Cited

U.S. PATENT DOCUMENTS

| | | | |
|---|---|---|---|
| 2,104,000 | 12/1937 | Reppe et al. | 526/332 |
| 2,104,002 | 12/1937 | Reppe et al. | 526/332 |
| 2,967,203 | 1/1961 | Nelson et al. | 252/52 R |
| 3,386,980 | 6/1968 | Lal et al. | 526/332 |
| 3,676,408 | 7/1972 | Schultz et al. | 526/332 |
| 4,944,890 | 7/1990 | Deeb et al. | 252/54 |
| 5,017,300 | 5/1991 | Raynolds | 252/67 |
| 5,032,306 | 7/1991 | Cripps | 252/68 |

*Primary Examiner*—Christine Skane
*Attorney, Agent, or Firm*—Antonelli, Terry, Stout & Kraus

[57] ABSTRACT

A lubricating oil for compression-type refrigerators which comprises as the main component thereof a polyvinyl ether compound having excellent compatibility with a hydrofluorocarbon or a hydrochlorofluorocarbon, such as 1,1,1,2-tetrafluoroethane and the like, which can be used as the refrigerant to replace compounds causing environmental pollution, such as dichlorofluoroethane and the like, and having an excellent lubricating property is disclosed. The lubricating oil for compression-type refrigerators comprises as the main component thereof a polyvinyl ether compound having the constituting units expressed by the general formula:

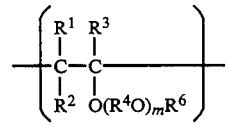

wherein $R^1$, $R^2$, $R^3$ are H or a hydrocarbon group of $C_{1\sim8}$, $R^4$ is a bivalent hydrocarbon group of $C_{2\sim10}$, $R^5$ is a hydrocarbon group of $C_{1\sim10}$ and m is $0\sim10$.

14 Claims, No Drawings

LUBRICATING OIL FOR COMPRESSION-TYPE REFRIGERATORS

BACKGROUND OF THE INVENTION

1. Field of the Invention

The present invention is related to a novel lubricating oil for compression-type refrigerators. More particularly, the present invention relates to a lubricating oil for compression-type refrigerators which comprises as the main component thereof a polyvinyl ether compound having excellent compatibility with hydrogen-containing Flon compounds ["a Flon compound" means a chlorofluorocarbon (CFC), a hydrofluorocarbon (HFC) and a hydrochlorofluorocarbon (HCFC) in general], such as 1,1,1,2-tetrafluoroethane, difluoromethane, pentafluoroethane (referred to as Flon 134a, Flon 32 and Flon 125, respectively, hereinafter) and the like, which can be used as the refrigerant to replace compounds causing environmental pollution, such as dichlorofluoroethane (referred to as Flon 12, hereinafter) and the like, and having an excellent lubricating property.

2. Description of the Related Arts

Compression-type refrigerators are generally constituted with a compressor, a condenser, an expansion valve and an evaporator and has a structure that mixed fluid of refrigerant and lubricating oil is circulated in this closed system. In the compression-type refrigerator generally temperature is high in the compressor and low in the refrigerator although the actual condition is different depending on kind of apparatus and it is generally required that the refrigerant and the lubricating oil are circulated in the system without causing phase separation in the wide range of temperature. When the phase separation occurs during the operation of the refrigerator, life and efficiency of the apparatus are adversely affected to a great extent. For example, when the phase separation of the refrigerant and the lubricating oil occurs in the part of the compressor, lubrication of the moving parts is deteriorated and seizure occurs to cause decrease of life of the apparatus to a great extent. When the phase separation occurs in the evaporator, efficiency of heat exchange is decreased because of the presence of lubricating oil of high viscosity.

Because the lubricating oil for refrigerators is used for the purpose of lubricating moving parts in refrigerators, the lubricating property is naturally important. Particularly, because the temperature in the compressor is high, the viscosity which can hold the oil film necessary for the lubrication is important. The required viscosity is different depending on the kind of the compressor used and conditions of use and it is generally preferable that viscosity (kinematic viscosity) of the lubricating oil before mixing with the refrigerant is 5 to 1000 cSt at 40° C. When the viscosity is lower than this range, oil film becomes thin to cause insufficient lubrication, and, when the viscosity is higher than this range, efficiency of the heat exchange is decreased.

Electric refrigerators have the motor and the compressor built into a single body and lubricating oil for them is required to have a high degree of electric insulating property. In general, volume specific resistance of $10^{12}$ Ω.cm or more at 80° C. is required. When the resistance is lower than this value, possibility of leak of electricity arises.

Furthermore, high degree of stability is required for lubricating oil. For example, when organic acids are formed by hydrolysis, corrosion and abrasion of apparatus tend to occur although degree of such occurrences depends on the amounts of the acids.

As the refrigerant for compressor-type refrigerators, mainly Flon 12 has heretofore been used and, as the lubricating oil, various kinds of mineral oil and synthetic oil satisfying the required properties described above have been used. However, Flon 12 is being more rigorously restricted world-wide because it brings environmental pollution such as the rupture of the ozone layer. By this reason, hydrogen-containing Flon compounds represented by Flon 134, Flon 32 and Flon 125 are attracting attention as the novel kinds of the refrigerant. The hydrogen-containing fluorocarbons, particularly Flon 134a, are preferred as the refrigerant for compression-type refrigerators because they have little possibility of causing the rupture of the ozone layer and can replace Flon 12 with little change of the structure of refrigerators which have heretofore been used.

When a hydrogen-containing Flon compound described above, such as Flon 134a and the like, is adopted as the refrigerant for compression-type refrigerators to replace Flon 12, a lubricating oil having good compatibility with the hydrogen-containing Flon compound, such as Flon 134a, Flon 32, Flon 125 and the like, and good lubricating property satisfying the requirements described above is naturally required. However, because the lubricating oils used in combination with Flon 12 heretofore do not have good compatibility with the hydrogen-containing Flon, such as Flon 134a, Flon 32, Flon 125 and the like, a new lubricating oil suited for these compounds is required. When a new lubricating oil is adopted in accordance with replacement of Flon 12, it is desired that major change of the structure of the apparatus is not necessary. It is not desirable that the structure of the currently used apparatus must have major changes because of a lubricating oil.

As the lubricating oil having the compatibility with Flon 134a, for example, lubricating oils of polyoxyalkylene glycols have been known. For example, Research Disclosure No. 17463 (October, 1978), the specification of the U.S. Pat. No. 4,755,316, Japanese Patent Application Laid Open No. 1989-256594, Japanese Patent Application Laid Open No. 1989-259093, Japanese Patent Application Laid Open No. 1989-259094, Japanese Patent Application Laid Open No. 1989-271491, Japanese Patent Application Laid Open No. 1990-43290, Japanese Patent Application Laid Open No. 1990-84491, Japanese Patent Applications Laid Open No. 1990-132176 to 132178, Japanese Patent Application Laid Open No. 1990-132179, Japanese Patent Application Laid Open No. 1990-173195, Japanese Patent Applications Laid Open No. 1990-180986 to 180987, Japanese Patent Applications Laid Open No. 1990-182780 to 182781, Japanese Patent Application Laid Open No. 1990-242888, Japanese Patent Application Laid Open No. 1990-258895, Japanese Patent Application Laid Open No. 1990-269195, Japanese Patent Application Laid Open No. 1990-272097, Japanese Patent Application Laid Open No. 1990-305893, Japanese Patent Application Laid Open No. 1991-28296, Japanese Patent Application Laid Open No. 1991-33193, Japanese Patent Applications Laid Open No. 1991-103496 to 103497, Japanese Patent Application Laid Open No. 1991-50297, Japanese Patent Application Laid Open No. 1991-52995, Japanese Patent Applications Laid Open No. 1991-70794 to 70795, Japanese Patent Application Laid Open No. 1991-79696, Japanese Patent Application Laid Open No. 1991-106992, Japanese Patent Application Laid Open No. 1991-109492, Japanese Patent Application Laid Open No. 1991-121195, Japanese Patent Application Laid Open No. 1991-205492, Japanese Patent Application Laid Open No. 1991-231992, Japanese Patent Application Laid Open No. 1991-231994, Japanese Patent Application Laid Open No. 1992-15295, Japanese Patent Application Laid Open No. 1992-39394 and Japanese Patent Applications Laid Open No. 1992-41591 to 41592 disclosed such lubricating oils. However, the lubricating oils of polyoxyalkylene glycols generally have low volume specific resistances and no example satisfying the value of $10^{12}$ $\Omega.cm$ or more at 80° C. has been disclosed yet.

As the compound having the compatibility with Flon 134a in addition to the lubricating oils of polyoxyalkylene glycols, lubricating oils of esters were disclosed in British Patent Laid Open No. 2216541, WO No. 6979 (1990), Japanese Patent Applications Laid Open No. 1990-276894, Japanese Patent Applications Laid Open No. 1991-128992, Japanese Patent Applications Laid Open No. 1991-88892, Japanese Patent Applications Laid Open No. 1991-179091, Japanese Patent Applications Laid Open No. 1991-252497, Japanese Patent Applications Laid Open No. 1991-275799, Japanese Patent Applications Laid Open No. 1992-4294, Japanese Patent Applications Laid Open No. 1992-20597 and the specification of the U.S. Pat. No. 5,021,179. However, it is inevitable that lubricating oils of esters form carboxylic acids by hydrolysis and this phenomenon causes corrosion of apparatuses. For example, rubber hoses are used in air conditioners of automobiles and lubricating oils of esters cannot be used because moisture penetrates through the rubber hoses. In electric refrigerators, although there is no possibility of penetration of moisture while they are used, lubricating oils are used for a long time without being changed to new oils and almost all amount of the moisture mixed at the time of production is used for hydrolysis, causing the problem. Because of these problems, a large extent of modification of the currently used apparatus or the apparatus for production is required when lubricating oils of esters for compression-type refrigerators is adopted and this situation is not desirable. As an oil for refrigerators having good resistance to hydrolysis, an oil composition for refrigerators characterized by containing an epoxy compound was disclosed in Japanese Patent Application Laid Open No. 1991-275799. However, the resistance to hydrolysis of this oil composition for refrigerators derives from the reaction of the epoxy group with water to form alcohol. When a large amount of water is contained, there is the possibility that the composition of the oil composition for refrigerators is changed to a large extent. Even when the content of water is small, the alcohol formed causes ester exchange reaction and there is the possibility that the composition of the oil composition for refrigerators is change to a large extent. Thus, this oil composition for refrigerators is not preferable.

Lubricating oils of carbonates were disclosed in Japanese Patent Application Laid Open No. 1991-149295, European Patent No. 421298, Japanese Patent Application Laid Open No. 1991-217495, Japanese Patent Application Laid Open No. 1991-247695, Japanese Patent Application Laid Open No. 1992-18490 and Japanese Patent Application Laid Open No. 1992-63893. However, the lubricating oils of carbonates have the same problem of hydrolysis as the lubricating oils of esters.

Thus, it is the real situation at present that a lubricating oil for the compression-type refrigerators having excellent compatibility with Flon 134a, excellent stability and lubricating property and a volume specific resistance at 80° C. of $10^{12}$ $\Omega.cm$ or more has not been discovered yet. Development of such a lubricant is strongly desired.

SUMMARY OF THE INVENTION

The present invention was undertaken in response with the desire described above with the object of providing a lubricating oil for compression-type refrigerators having excellent compatibility in the whole range of the temperature of application with hydrogen-containing Flon compounds, such as Flon 134a, Flon 32, Flon 125 and the like, which can replace the refrigerant of Flon 12 or other Flon compounds that are hardly decomposed and cause the problem of environmental pollution, having excellent stability and lubricating property and having a volume specific resistance at 80° C. of $10^{12}$ $\Omega.cm$ or more.

As the result of the intensive studies by the present inventors for developing the lubricating oil for compression-type refrigerators having the desirable properties described above, it was discovered that the object can be achieved by a lubricating oil comprising a polyvinyl ether compound having a specific structure as the main component thereof. The present invention was completed on the basis of this discovery.

Thus, the present invention provides a lubricating oil for compression-type refrigerators which comprises as the main component thereof a polyvinyl ether compound having the constituting unit expressed by the general formula (I):

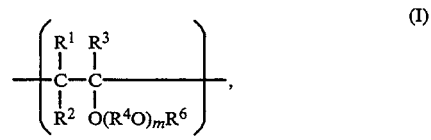

wherein $R^1$, $R^2$ and $R^3$ are a hydrogen atom or a hydrocarbon group having 1 to 8 carbon atoms, respectively, and may be the same or different from each other, $R^4$ is a bivalent hydrocarbon group having 2 to 10 carbon atoms, $R^5$ is a hydrocarbon group having 1 to 10 carbon atoms, m is a number the average of which is in the range of 0 to 10, $R^1$ to $R^5$ may be the same or different between the constituting units and a plural of $R^4O$'s may be the same or different from each other when a plural of $R^4O$'s are comprised.

DESCRIPTION OF PREFERRED EMBODIMENTS

The lubricating oil for compression-type refrigerators of the present invention comprises as the main component thereof a polyvinyl ether compound having the constituting unit expressed by the general formula (I):

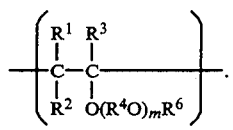

(I)

In the general formula (I), $R^1$, $R^2$ and $R^3$ are a hydrogen atom or a hydrocarbon group having 1 to 8 carbon atoms, respectively, and may be the same or different from each other. The hydrocarbon group described above is more specifically an alkyl group, such as methyl group, ethyl group, n-propyl group, isopropyl group, n-butyl group, isobutyl group, sec-butyl group, tert-butyl group, various kinds of pentyl group, various kinds of hexyl group, various kinds of heptyl group and various kinds of octyl group; a cycloalkyl group, such as cyclopentyl group, cyclohexyl group, various kinds of methylcyclohexyl group, various kinds of ethylcyclohexyl group, various kinds of dimethylcyclohexyl group and the like; an aryl group, such as phenyl group, various kinds of methylphenyl group, various kinds of ethylphenyl group and various kinds of dimethylphenyl group; or an arylalkyl group, such as benzyl group, various kinds of phenylethyl group and various kinds of methylbenzyl group. $R^1$, $R^2$ and $R^3$ are preferably a hydrogen atom or an aliphatic hydrocarbon group having 5 or less carbon atoms, respectively, and more preferably a hydrogen atom or a hydrocarbon group having 3 or less carbon atoms, respectively.

$R^4$ in the general formula (I) is a bivalent hydrocarbon group having 2 to 10 carbon atoms. The bivalent hydrocarbon group having 2 to 10 carbon atoms is more specifically a bivalent aliphatic group, such as ethylene group, phenylethylene group, 1,2-propylene group, 2-phenyl-1,2-propylene group, 1,3-propylene group, various kinds of butylene group, various kinds of pentylene group, various kinds of hexylene group, various kinds of heptylene group, various kinds of octylene group, various kinds of nonylene group and various kinds of decylene group; an alicyclic group having two bonding positions on an alicyclic hydrocarbon, such as cyclohexane, methylcyclohexane, ethylcyclohexane, dimethylcyclohexane, propylcyclohexane and the like; a bivalent aromatic hydrocarbon, such as various kinds of phenylene group, various kinds of methylphenylene group, various kinds of ethylphenylene group, various kinds of dimethylphenylene group, various kinds of naphthylene group and the like; an alkylaromatic group having one univalent bonding position on each of the alkyl part and the aromatic part of an alkylaromatic hydrocarbon, such as toluene, xylene, ethylbenzene and the like; or an alkylaromatic group having bonding positions on the parts of alkyl groups of a polyalkylaromatic hydrocarbon, such as xylene, diethylbenzene and the like. The aliphatic group having 2 to 4 carbon atoms is particularly preferable among them. A plural of $R^4O$'s may be the same or different from each other.

In the general formula (I), m shows the number of repeating and the average of k is in the range of 0 to 10 and preferably in the range of 0 to 5.

In the general formula (I), $R^5$ is a hydrocarbon group having 1 to 10 carbon atoms, which is more specifically an alkyl group, such as methyl group, ethyl group, n-propyl group, isopropyl group, n-butyl group, isobutyl group, sec-butyl group, tert-butyl group, various kinds of pentyl group, various kinds of hexyl group, various kinds of heptyl group, various kinds of octyl group, various kinds of nonyl group and various kinds of decyl group; a cycloalkyl group, such as cyclopentyl group, cyclohexyl group, various kinds of methylcyclohexyl group, various kinds of ethylcyclohexyl group, various kinds of propylcyclohexyl group, various kinds of dimethylcyclohexyl group and the like; an aryl group, such as phenyl group, various kinds of methylphenyl group, various kinds of ethylphenyl group, various kinds of dimethylphenyl group, various kinds of propylphenyl group, various kinds of trimethylphenyl group, various kinds of butylphenyl group, various kinds of naphthyl group and the like; or an arylalkyl group, such as benzyl group, various kinds of phenylethyl group, various kinds of methylbenzyl group, various kinds of phenylpropyl group and various kinds of phenylbutyl group. The hydrocarbons having 8 or less carbon atoms are preferable among them. When m is 0, an alkyl group having 1 to 6 carbon atoms is particularly preferable and, when m is 1 or more, an alkyl group having 1 to 4 carbon atoms is particularly preferable.

The polyvinyl ether compound of the present invention comprises the repeating unit expressed by the general formula (I). The number of repeating which is the degree of polymerization can be suitably selected according to the desired kinematic viscosity. The kinematic viscosity is generally in the range of 5 to 1000 cSt (40° C.) and preferably in the range of 5 to 800 cSt (40° C.).

The polyvinyl ether compound of the present invention can be produced by polymerization of the corresponding vinyl ether monomer. The vinyl ether monomer which can be used here is the compound expressed by the general formula (VI):

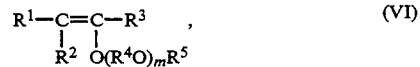

(VI)

wherein $R^1$, $R^2$, $R^3$, $R^4$, $R^5$ and m are the same as those described above. As the vinyl ether monomer, various compounds corresponding to the polyvinyl ether compounds described above can be mentioned. Examples of the vinyl ether monomer expressed by the general formula are: vinyl methyl ether, vinyl ethyl ether, vinyl n-propyl ether, vinyl isopropyl ether, vinyl n-butyl ether, vinyl isobutyl ether, vinyl sec-butyl ether, vinyl tert-butyl ether, vinyl n-pentyl ether, vinyl n-hexyl ether, vinyl 2-methoxyethyl ether, vinyl 2-ethoxyethyl ether, vinyl 2-methoxy-1-methylethyl ether, vinyl 2-methoxypropyl ether, vinyl 3,6-dioxaheptyl ether, vinyl 3,6,9-trioxadecyl ether, vinyl 1,4-dimethyl-3,6-dioxaheptyl ether, vinyl 1,4,7-trimethyl-3,6,9-trioxadecyl ether, vinyl 2,6-dioxa-4-heptyl ether, vinyl 2,6,9-trioxa-4-decyl ether, 1-methoxypropene, 1-ethoxypropene, 1-n-propoxypropene, 1-isopropoxypropene, 1-n-butoxypropene, 1-isobutoxypropene, 1-sec-butoxypropene, 1-tert-butoxypropene, 2-methoxypropene, 2-ethoxypropene, 2-n-propoxypropene, 2-isopropoxypropene, 2-n-butoxypropene, 2-isobutoxypropene, 2-sec-butoxypropene, 2-tert-butoxypropene, 1-methoxy-1-butene, 1-ethoxy-1-butene, 1-n-propoxy-1-butene, 1-isopropoxy-1-butene, 1-n-butoxy-1-butene, 1-isobutoxy-1-butene, 1-sec-butoxy-1-butene, 1-tert-butoxy-1-butene, 2-methoxy-1-butene, 2-ethoxy-1-butene, 2-n-propoxy-1-butene, 2-isopropoxy-1-butene, 2-n-butoxy-1-butene, 2-isobutoxy-1-butene, 2-sec-butoxy-1-butene, 2-tert-butoxy-1-butene, 2-methoxy-2-butene, 2-ethoxy-2-butene, 2-n-propoxy-2-butene, 2-isopropoxy-2-butene, 2-n-butoxy-2-butene, 2-isobutoxy-2-butene, 2-sec-butoxy-2-butene, 2-tert-butoxy-2-butene and the like. These vinyl ethers can be produced by conventional methods.

The ends of the polyvinyl ether compound comprising the constituting units express by the general formula (I) which is used in the lubricating oil of the present invention as the main component thereof can be converted to the desired structure by the method disclosed in the examples of the present invention or by the conventional methods. The group to be converted to is a saturated hydrocarbon, an ether, an alcohol, a ketone, an amide, a nitrile or the like.

As the polyvinyl ether compound which is the main component of the lubricating oil of the present invention, the compounds having the end structures shown in the following are preferably utilized:

(1) The structure in which one end is expressed by the general formula (II):

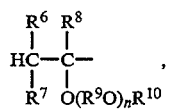
(II)

wherein $R^6$, $R^7$ and $R^8$ are a hydrogen atom or a hydrocarbon group having 1 to 8 carbon atoms, respectively, and may be the same or different from each other, $R^9$ is a bivalent hydrocarbon group having 2 to 10 carbon atoms, $R^{10}$ is a hydrocarbon group having 1 to 10 carbon atoms, n is a number the average of which is in the range of 0 to 10 and a plural of $R^9O$'s may be the same or different from each other when a plural of $R^9O$'s are comprised, and the other end is expressed by (III):

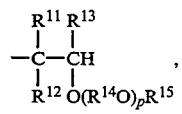
(III)

wherein $R^{11}$, $R^{12}$ and $R^{13}$ are a hydrogen atom or a hydrocarbon group having 1 to 8 carbon atoms, respectively, and may be the same or different from each other, $R^{14}$ is a bivalent hydrocarbon group having 2 to 10 carbon atoms, $R^{15}$ is a hydrocarbon group having 1 to 10 carbon atoms, p is a number the average of which is in the range of 0 to 10 and a plural of $R^{14}O$'s may be the same or different from each other when a plural of $R^{14}O$'s are comprised;

(2) The structure in which one end of the polyvinyl ether compound is expressed by the general formula (II) and the other end is expressed by the general formula (IV):

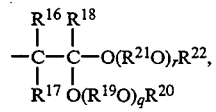
(IV)

wherein $R^{16}$, $R^{17}$ and $R^{18}$ are a hydrogen atom or a hydrocarbon group having 1 to 8 carbon atoms, respectively, and may be the same or different from each other, $R^{19}$ and $R^{21}$ are a bivalent hydrocarbon group having 2 to 10 carbon atoms, respectively, and may be the same or different from each other, $R^{20}$ and $R^{22}$ are a hydrocarbon group having 1 to 10 carbon atoms, respectively, and may be the same or different from each other, q and r are a number the average of which is in the range of 0 to 10, respectively, and may be the same or different from each other, a plural of $R^{19}O$'s may be the same or different from each other when a plural of $R^{19}O$'s are comprised and a plural of $R^{21}O$'s may be the same or different from each other when a plural of $R^{21}O$'s are comprised;

(3) The structure in which one end of the polyvinyl ether compound is expressed by the general formula (II) and the other end has the structure comprising an olefinic unsaturated bond; and (4) The structure in which one end of the polyvinyl ether compound is expressed by the general formula (II) and the other end is expressed by the general formula (V):

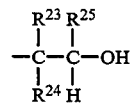
(V)

wherein $R^{23}$, $R^{24}$ and $R^{25}$ are a hydrogen atom or a hydrocarbon group having 1 to 8 carbon atoms, respectively, and may be the same or different from each other.

The polyvinyl ether compound may be a mixture of two or more compounds having the end structures selected from the group consisting of the structures (1) to (4). The preferable examples of such mixture are a mixture of the compound having the structure (1) and the compound having the structure (4) and a mixture of the compound having the structure (2) and the compound having the structure (3).

The lubricating oil of the present invention comprises the polyvinyl ether compound described above as the main component thereof. Because the kinematic viscosity of the lubricating oil before mixing with the refrigerant is preferably in the range of 5 to 1000 cSt at 40° C., the materials described above, the initiator and the conditions of the reaction are preferably selected in such a manner that the polyvinyl ether compound having the kinematic viscosity in this range is formed. The average molecular weight of this polymer is generally in the range of 150 to 4000. When kinematic viscosity of a polymer is out of the specified range, the kinematic viscosity can be adjusted to the specified range by mixing with another polymer having a suitable kinematic viscosity.

In the lubricating oil for refrigerators of the present invention, the polyvinyl ether compound described above may be utilized singly or as a combination of two or more kinds. It may be utilized by mixing with other kinds of lubricating oils as well.

In the lubricating oil for refrigerators of the present invention, various kinds of additives utilized in conventional lubricating oils, such as load resistant additives, chlorine capturing agents, antioxidants, metal deactivators, defoaming agents, detergent-dispersants, viscosity-index improvers, oiliness agents, anti-wear additives, extreme pressure agents, antirust agents, corrosion inhibitors, pour point depressants and the like, may be added according to desire.

Examples of the load resistant additives described above are: organic sulfur compound additives, such as monosulfides, polysulfides, sulfoxides, sulfones, thiosulfinates, sulfurized oils and fats, thiocarbonates, thiophenes, thiazoles, methanesulfonic acid esters and the like; phosphoric ester additives, such as phosphoric monoesters, phosphoric diesters, phosphoric triesters (tricresyl phosphate) and the like; phosphorous ester additives, such as phosphorous monoesters, phosphorous diesters, phosphorous triesters and the like; thiophosphoric ester additives, such as thiophosphoric triesters; fatty acid ester additives, such as higher fatty acids, hydroxyaryl fatty acids, esters of polyhydric alcohols containing carboxylic acids, acrylic esters and the like; organic chlorine additives, such as chlorinated hydrocarbons, chlorinated carboxylic acid derivatives and the like; organic fluorine additives, such as fluorinated aliphatic carboxylic acids, fluoroethylene resins, fluoroalkyl polysiloxanes, fluorinated graphite and the like; alcohol additives, such as higher alcohols and the like; and metallic compound additives, such as salts of naphthenic acid (lead naphthenate), salts of fatty acids (lead salts of fatty acids), salts of thiophosphates (zinc dialkyl dithiophosphates), salts of thiocarbamic acid, organomolybdenum compounds, organotin compounds, organo-germanium compounds, boric acid esters and the like.

Examples of the chlorine capturing agents are compounds having glycidyl ether group, epoxy fatty acid monoesters, epoxidized fats and oils, compounds having epoxycycloalkyl group and the like. Examples of the antioxidants are phenols (2,6-di-tert-butyl-p-cresol), aromatic amines (α-naphthylamine) and the like. Examples of the metal deactivators are benzotriazole derivatives and the like. Examples of the defoaming agents are silicone oil (dimethylpolysiloxane), polymethacrylates and the like. Examples of the detergent dispersants are sulfonates, phenates, succinimides and the like. Examples of the viscosity index improvers are polymethacrylates, polyisobutylene, ethylene-propylene copolymers, hydrogenated styrene-diene copolymers and the like.

The lubricating oil of the present invention is utilized as the lubricating oil for compression-type refrigerators because of the excellent compatibility with the refrigerants and the excellent lubricating property. Unlike the conventional lubricating oils, the lubricating oil of the present invention has excellent compatibility with hydrogen-containing Flon compounds, such as Flon 134a and the like [more specifically, 1,1-dichloro-2,2,2-trifluoroethane (Flon 123), 1-chloro-1,1-difluoroethane (Flon 142b), 1,1-difluoroethane (Flon 152a), chlorodifluoromethane (Flon 22), trifluoromethane (Flon 23), difluoromethane (Flon 32), pentafluoroethane (Flon 125) and the like in addition to Flon 134a described above] which can be used to replace Flon 12 or other Flon compounds used as refigerants and not easily decomposed to cause environmental pollution.

The lubricating oil of the present invention can be utilized by mixing with other lubricating oils for compression-type refrigerators for the purpose of improving the compatibility of the other lubricating oils with the refrigerant.

The lubricating oil of the present invention has excellent stability and lubricating property and a volume specific resistance at 80° C. of $10^{12}$ Ω.cm or more and is favorably used as the lubricating oil for compression-type refrigerators.

The present invention is described with reference to examples and comparative examples in more detail in the following. However, the present invention is not limited by the examples and the comparative examples.

Example of Catalyst Preparation 1

Into a flask, 100 g (containing water) of Raney nickel (a product of Kawaken Fine Chemical Co., Ltd., M300T) was charged and 100 g of absolute ethanol was added to it and mixed well. The mixture was left standing to have Raney nickel precipitated and the supernatant liquid was removed by decantation. The Raney nickel remaining in the flask was repeatedly treated with the treatment described above 5 times.

Raney nickel used in Examples of Preparation was the material obtained in this Example of Catalyst Preparation which was wet with ethanol.

Examples of Catalyst Preparation 2

Into a 100 ml flask of egg-plant type, 20 g of zeolite (a product of Toso Co., Ltd., HSZ330HUA) was charged. The flask was then dipped in an oil bath of 150° C. and evacuated by an oil rotary vacuum pump for 1 hour. After cooling to the room temperature, the flask was brought to the atmospheric pressure by introducing dry nitrogen.

Zeolite used in Examples of Preparation was the material obtained in this Example of Catalyst Preparation.

Example of Preparation 1

Into a 5 liter glass flask equipped with a dropping funnel, a cooler and a stirrer, 600 g of ethyl vinyl ether, 72 g of methanol and 2400 g of hexane were charged and cooled with water under stirring. When the temperature reached 5° C., a solution prepared by dissolving 3.6 g of boron trifluoride diethyl etherate in 20 g of tetrahydrofuran was added and the mixture was stirred for 1 hour. During this period, the reaction started and the temperature of the reaction increased. Refluxing of ethyl vinyl ether was observed in the cooler. The reaction mixture was transferred to a washing vessel and washed with 1500 ml of a 3 weight % aqueous solution of sodium hydroxide 3 times, then with 1500 ml of water 3 times. The product was concentrated by using a rotary evaporator and dried under the reduced pressure (0.2 mmHg) at 50° C. for 1 hour to obtain 468 g of the crude product.

Into a 5 liter glass flask equipped with a dropping funnel, a cooler and a stirrer, 400 g of the crude product obtained above, 500 g of acetone, 800 g of water and 10 g of concentrated hydrochloric acid (35 weight %) were charged and stirred at 50° to 60° C. for 3 hours. After hydrochloric acid was neutralized with sodium hydrogen carbonate, acetone and the like was removed under the reduced pressure by using a rotary evaporator and the remaining product was poured into 400 ml of hexane. After removing the aqueous phase, the product was washed with 400 ml of water once. The hexane phase was transferred to an autoclave and hydrogenated by using 0.8 g of a platinum oxide as catalyst at the hydrogen pressure of 20 kg/cm² at 50° C. for 1 hour. After removing the platinum oxide by filtration, the product was transferred to a 2 liter glass flask, added with 40 g of methanol and 8 g of sodium borohydride and stirred for 1 hour at the room temperature. The product was made weakly acidic with an aqueous solution of acetic acid and then acetic acid was neutralized with sodium hydrogen carbonate. The product was washed with 400 ml of water once and the solvent and water were removed under the reduced pressure by using a rotary evaporator.

The residual product thus obtained was dissolved in 300 ml of tetrahydrofuran and the reaction with 12 g of sodium hydride was conducted for 1 hour. Generation of hydrogen gas was observed during this reaction. Then, 120 g of methyl iodide was dropped in 30 minutes to the reaction mixture. Generation of heat was observed during this period. After dropping methyl iodide, the reaction mixture was stirred for further 1 hour. The solvent and unreacted materials were removed under the reduced pressure by using a rotary evaporator. The residue was transferred to a 2 liter washing vessel and, after being dissolved into 400 ml of hexane, washed with 400 ml of water 5 times. Then, after adding 40 g of an ion exchange resin, the product was stirred for 3 hours. The ion exchange resin was removed by filtration and hexane was removed from the product under the reduced pressure by using a rotary evaporator. The yield of the lubricating oil of the present invention thus obtained was 200 g.

The nuclear magnetic resonance spectrum (abbreviated as NMR in the following description) and the infrared absorption spectrum (abbreviated as IR in the following description) of the product were measured and it was shown that one of the end structures of the polymer was (A) and the other was (B):

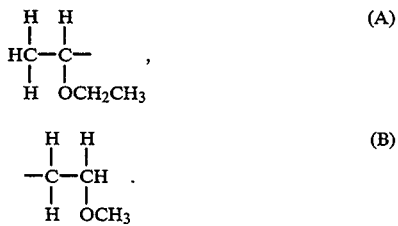

Example of Preparation 2

Into a 5 liter glass flask equipped with a dropping funnel, a cooler and a stirrer, 600 g of ethyl vinyl ether, 60 g of methanol and 2400 g of hexane were charged and cooled with water under stirring. When the temperature reached 5° C., a solution prepared by dissolving 3.6 g of boron trifluoride diethyl etherate in 20 g of tetrahydrofuran was added and the mixture was stirred for 1 hour. During this period, the reaction started and the temperature of the reaction increased. Refluxing of ethyl vinyl ether was observed in the cooler. The reaction mixture was transferred to a washing vessel and washed with 1500 ml of a 3 weight % aqueous solution of sodium hydroxide 3 times, then with 1500 ml of water 3 times. The product was concentrated by using a rotary evaporator and dried under the reduced pressure (0.2 mmHg) at 50° C. for 1 hour to obtain 452 g of the crude product.

Into a 5 liter glass flask equipped with a dropping funnel, a cooler and a stirrer, 400 g of the crude product obtained above, 500 g of acetone, 800 g of water and 10 g of a concentrated hydrochloric acid (35 weight %) were charged and stirred at 50° to 60° C. for 3 hours. After hydrochloric acid was neutralized with sodium hydrogen carbonate, acetone and the like was removed under the reduced pressure by using a rotary evaporator and the remaining product was poured into 400 ml of hexane. After removing the aqueous phase, the product was washed with 400 ml of water once. The hexane phase was transferred to an autoclave and hydrogenated by using 0.8 g of a platinum oxide as catalyst at the hydrogen pressure of 20 kg/cm$^2$ at 50° C. for 1 hour. After removing the platinum oxide by filtration, the product was transferred to a 2 liter glass flask, added with 40 g of methanol and 8 g of sodium borohydride and stirred for 1 hour at the room temperature. The product was made weakly acidic with an aqueous solution of acetic acid and then acetic acid was neutralized with sodium hydrogen carbonate. The product was washed with 400 ml of water once and the solvent and water were removed under the reduced pressure by using a rotary evaporator.

The residual product thus obtained was dissolved in 300 ml of tetrahydrofuran and the reaction with 12 g of sodium hydride was conducted for 1 hour. Generation of hydrogen gas was observed during this reaction. Then, 120 g of methyl iodide was dropped in 30 minutes to the reaction mixture. Generation of heat was observed during this period. After dropping methyl iodide, the reaction mixture was stirred for further 1 hour. The solvent and unreacted materials were removed under the reduced pressure by using a rotary evaporator. The residue was transferred to a 2 liter washing vessel and, after being dissolved into 400 ml of hexane, washed with 400 ml of water 5 times. Then, after adding 40 g of an ion exchange resin, the product was stirred for 3 hours. The ion exchange resin was removed by filtration and hexane was removed from the product under the reduced pressure by using a rotary evaporator. The yield of the lubricating oil of the present invention thus obtained was 208 g.

NMR and IR of the product were measured and it was shown that one of the end structures of the polymer was (A) and the other was (B).

Example of Preparation 3

Into a 5 liter glass flask equipped with a dropping funnel, a cooler and a stirrer, 500 g of hexane was charged, a solution prepared by dissolving 12 g of boron trifluoride diethyl etherate in 24 g of tetrahydrofuran was added to it and the mixture was cooled to 5° C. with an ice water bath. In a dropping funnel, 2000 g of ethyl vinyl ether and 120 g of methanol were charged and the mixture was dropped in 1 hour and 30 minutes. During this period, the reaction started and the temperature of the reaction increased. The temperature was kept at about 30° C. by cooling with the ice water bath. After finishing the dropping, the stirring was kept for further 30 minutes. The reaction mixture was transferred to a washing vessel and washed with 1500 ml of a 3 weight % aqueous solution of sodium hydroxide 3 times, then with 1500 ml of water 3 times. The solvent and unreacted materials were removed under the reduced pressure by using a rotary evaporator to obtain 1806 g of the crude product.

Into a 2 liter glass flask equipped with a dropping funnel, a cooler and a stirrer, 400 g of the crude product obtained above and 300 g of tetrahydrofuran were charged and then 15 g of lithium aluminum hydride was added to the mixture, followed by stirring for 30 minutes. In a dropping funnel, 196 g of boron trifluoride diethyl etherate was charged and dropped in 1 hour. During the dropping, generation of heat was observed and the temperature was kept at 10° to 20° C. by cooling with an ice water bath. The reaction mixture was further stirred for 30 minutes after finishing the dropping and then neutralized by adding sodium hydroxide. The precipitate thus obtained was removed by filtration and the liquid phase was treated with a rotary evaporator to remove the alcohol produced, the solvent and water under the reduced pressure. The remaining product was transferred to a 2 liter washing vessel and dissolved into 500 ml of hexane. The solution was washed with 200 ml of a 5 weight % aqueous solution of sodium hydroxide 10 times and then with 200 ml of water 3 times. To the solution, 100 g of an ion exchange resin was added and the mixture was stirred for 3 hours. After removing the ion exchange resin by filtration, hexane was removed under the reduced pressure by using a rotary evaporator. The yield of the lubricating oil of the present invention was 235 g.

NMR and IR of the product were measured and it was shown that one of the end structures of the polymer was (A) and the other was a mixture of (B) and (C):

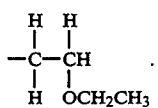
(C)

Example of Preparation 4

Into a 5 liter glass flask equipped with a dropping funnel, a cooler and a stirrer, 1000 g of toluene, 500 g of acetaldehyde diethyl acetal and 5.0 g of boron trifluoride diethyl etherate were charged. Into a dropping funnel, 2500 g of ethyl vinyl ether was charged and dropped in 2 hours and 30 minutes. During this period, the reaction started and the temperature of the reaction increased. The temperature was kept at about 25° C. by cooling with an ice water bath. After finishing the dropping, the solution was further stirred for 5 minutes. The reaction mixture was transferred to a washing vessel and washed with 1000 ml of a 5 weight % aqueous solution of sodium hydroxide 3 times and then with 1000 ml of water 3 times. The solvent and unreacted materials were removed under the reduced pressure by using a rotary evaporator to obtain 2833 g of the crude product.

Into a 2 liter autoclave made of SUS-316L, 600 g of the crude product, 600 g of hexane, 60 g of Raney nickel and 60 g of zeolite were charged. Hydrogen was introduced into the autoclave and the pressure of hydrogen was adjusted to 20 kg/cm². After stirring for about 30 seconds, the pressure was released. Hydrogen was introduced into the autoclave again to make the pressure of hydrogen 20 kg/cm² and, after stirring for about 30 seconds, the pressure of hydrogen was released. After repeating this operation once more, the pressure of hydrogen was increased to 50 kg/cm² and the temperature was increased to 130° C. in 30 minutes under stirring. The reaction was conducted at 130° C. for 1 hour. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm² during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 100 ml of hexane twice. The washing liquid was combined with the reaction liquid and filtered with filter paper. The combined liquid was then transferred to a washing vessel and washed with 500 ml of a 5 weight % aqueous solution of sodium hydroxide 3 times and then with 500 ml of distilled water 5 times. Hexane, water and the like were removed under the reduced pressure by using a rotary evaporator. The yield was 468 g.

NMR and IR of the product were measured and it was shown that one of the end structures of the polymer was (A) and the other was a mixture of (C) and (D), in which (C) was the major structure and (D) was the minor structure.

Example of Preparation 5

By using the catalyst recovered by decantation in Example of Preparation 4, the reaction was conducted with 600 g of the crude product prepared in Example of Preparation 4 by the same method as in Example of Preparation 4. The yield was 501 g.

It was shown that the catalyst could be recycled further.

NMR and IR of the product were measured and it was shown that one of the end structures of the polymer was (A) and the other was a mixture of (C) and (D), in which (C) was the major structure and (D) was the minor structure.

Example of Preparation 6

Into a 1 liter glass flask equipped with a dropping funnel, a cooler and a stirrer, 250 g of toluene, 36.82 g of isopropyl alcohol and 4.35 g of boron trifluoride diethyl etherate were charged. Into a dropping funnel, 500 g of isopropyl vinyl ether was charged and dropped in 30 minutes. During this period, the reaction started and the temperature of the reaction solution increased. The temperature was kept at about 30° C. by cooling with an ice water bath. After finishing the dropping, the solution was further stirred for 5 minutes. The reaction mixture was transferred to a washing vessel and washed with 130 ml of a 3 weight % aqueous solution of sodium hydroxide 3 times and then with 200 ml of water 3 times. The solvent and unreacted materials were removed under the reduced pressure by using a rotary evaporator to obtain 475.3 g of the crude product.

Into a 1 liter autoclave made of SUS-316L, 380 g of the crude product, 100 g of hexane, 45 g of Raney nickel and 45 g of zeolite were charged. Hydrogen was introduced into the autoclave and the pressure of hydrogen was adjusted to 20 kg/cm². After stirring for about 30 seconds, the pressure was released. Hydrogen was introduced into the autoclave again to make the pressure of hydrogen 20 kg/cm² and, after stirring for about 30 seconds, the pressure of hydrogen was released. After repeating this operation once more, the pressure of hydrogen was increased to 50 kg/cm² and the temperature was increased to 130° C. in 30 minutes under stirring. The reaction was conducted at 130° C. for 1 hour. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm$^2$ during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 100 ml of hexane twice. The washing liquid was combined with the reaction liquid and filtered with filter paper. The catalyst could be used by recycling further. The combined liquid was then transferred to a washing vessel and washed with 200 ml of a 5 weight % aqueous solution of sodium hydroxide 3 times and then with 200 ml of distilled water 5 times. Hexane, water and the like were removed under the reduced pressure by using a rotary evaporator. The yield was 287 g.

NMR and IR of the product were measured and it was shown that one of the end structures of the polymer was (E) and the other was a mixture of (F) and (D), in which (F) was the major structure and (D) was the minor structure.

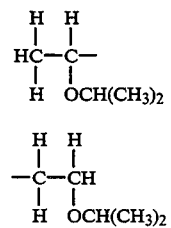

increased to 50 kg/cm$^2$ and the temperature was increased to 130° C. in 30 minutes under stirring. The reaction was conducted at 130° C. for 1 hour. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm$^2$ during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 50 ml of hexane twice. The washing liquid was combined with the reaction liquid and filtered with filter paper. Hexane was removed under the reduced pressure by using a rotary evaporator and 300 g of chloroform was added. The liquid was then transferred to a washing vessel and washed with 100 ml of a 5 weight % aqueous solution of sodium hydroxide 3 times and then with 100 ml of distilled water 5 times. Chloroform, water and the like were removed under the reduced pressure by using a rotary evaporator. The yield was 150 g.

NMR and IR of the product were measured and it was shown that one of the end structures of the polymer was (G) and the other was a mixture of (B) and (D), in which (B) was the major structure and (D) was the minor structure.

Example of Preparation 7

Into a 1 liter autoclave, 200 g of toluene, 5.5 g of methanol and 1.2 g of boron trifluoride diethyl etherate were charged and the atmosphere inside of the autoclave was replaced with nitrogen. While the content of the autoclave was stirred, 200 g of methyl vinyl ether was added with pressure in 4 hours. During this period, the reaction started and the generation of heat was observed. The reaction was conducted while the temperature in the autoclave was kept at about 5° C. by cooling the autoclave with an ice water bath. After finishing the addition of methyl vinyl ether with pressure, the solution was further stirred for 5 minutes. The reaction mixture was transferred to a washing vessel and washed with 100 ml of a 5 weight % aqueous solution of sodium hydroxide 3 times and then with 100 ml of water 3 times. The solvent and unreacted materials were removed under the reduced pressure by using a rotary evaporator to obtain 165 g of the crude product.

Into an autoclave, 165 g of the crude product, 200 g of hexane, 15 g of Raney nickel and 15 g of zeolite were charged. Hydrogen was introduced into the autoclave and the pressure of hydrogen was adjusted to 20 kg/cm$^2$. After stirring for about 30 seconds, the pressure was released. Hydrogen was introduced into the autoclave again to make the pressure of hydrogen 20 kg/cm$^2$ and, after stirring for about 30 seconds, the pressure of hydrogen was released. After repeating this operation once more, the pressure of hydrogen was

Example of Preparation 8

Into a 5 liter glass flask equipped with a dropping funnel, a cooler and a stirrer, 1000 g of toluene, 500 g of acetaldehyde diethyl acetal and 5.0 g of boron trifluoride diethyl etherate were charged. Into a dropping funnel, 2500 g of ethyl vinyl ether was charged and dropped in 2 hours and 30 minutes. During this period, the reaction started and the temperature of the reaction solution increased. The temperature was kept at about 25° C. by cooling with an ice water bath. After finishing the dropping, the solution was further stirred for 5 minutes. The reaction mixture was transferred to a washing vessel and washed with 1000 ml of a 5 weight % aqueous solution of sodium hydroxide 3 time and then with 1000 ml of water 3 times. The solvent and unreacted materials were removed under the reduced pressure by using a rotary evaporator to obtain 2833 g of the crude product.

NMR and IR of the product were measured and it was shown that one of the end structures of the polymer was (A) and the other was a mixture of (H) and (I), in which the ratio (H)/(I) was 1/4.5.

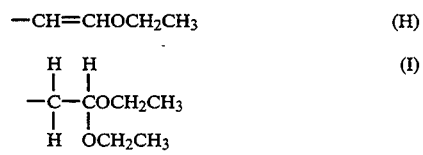

Example of Preparation 9

Into a 2 liter autoclave made of SUS-316L, 700 g of the polymer of ethyl vinyl ether obtained in Example of Preparation 8, 35 g of Raney nickel, 35 g of zeolite and 1.5 g of water were charged. Hydrogen was introduced into the autoclave and the pressure of hydrogen was adjusted to 10 kg/cm$^2$. After stirring for about 30 seconds, the pressure was released. Hydrogen was introduced into the autoclave again to make the pressure of hydrogen 10 kg/cm$^2$ and, after stirring for about 30 seconds, the pressure of hydrogen was released. After repeating this operation once more, the pressure of hydrogen was increased to 35 kg/cm$^2$ and the temperature was increased to 140° C. in 30 minutes under stirring. The reaction was conducted at 140° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 35 kg/cm$^2$ during the reaction. After finishing the reaction, the reaction mixture was cooled to the room temperature and the pressure was decreased to the atmospheric pressure. The reaction product was filtered with filter paper. The reaction product was then transferred to a 2 liter washing vessel, diluted with 300 g of hexane and washed with 250 ml of a 5 weight % aqueous solution of sodium hydroxide 3 times and then with 250 ml of distilled water 5 times. Hexane, water and the like were removed under the reduced pressure by using a rotary evaporator. The yield was 550 g. NMR and IR of the product were measured and it was shown that one of the end structures of the polymer was (A) and the other was a mixture of (C) and (D).

Example of Preparation 10

Into a 500 ml glass flask equipped with a dropping funnel, a cooler and a stirrer, 50 g of toluene, 17.7 g of acetaldehyde diethyl acetal and 1.5 g of boron trifluoride diethyl etherate were charged. Into a dropping funnel, 43 g of ethyl vinyl ether and 65 g of isopropyl vinyl ether were charged and dropped in 50 minutes. The temperature of the reaction solution increased by the heat of reaction and the temperature was kept at about 30° C. by cooling with an ice water bath. After finishing the dropping, the solution was further stirred for 5 minutes. The reaction mixture was transferred to a washing vessel and washed with 100 ml of a 5 weight % aqueous solution of sodium hydroxide 3 times and then with 150 ml of water 3 times. The solvent and unreacted materials were removed under the reduced pressure by using a rotary evaporator to obtain 120 g of the crude product. The crude product had the kinematic viscosity of 48.8 cSt at 40° C. NMR and IR of the product were measured and it was shown that one of the end structures of the polymer was a mixture of (A) and (E) and the other was a mixture of (H), (I) and structures in which the oxyethyl groups in (H) and (I) are replaced by an oxyisopropyl group, respectively.

Example of Preparation 11

Into a 1 liter autoclave made of SUS-316L, 110 g of the copolymer of ethyl vinyl ether and isopropyl vinyl ether obtained in Example of Preparation 10, 300 g of hexane, 5.5 g of Raney nickel and 5.5 g of zeolite were charged. Hydrogen was introduced into the autoclave and the pressure of hydrogen was adjusted to 20 kg/cm$^2$. After stirring for about 30 seconds, the pressure was released. Hydrogen was introduced into the autoclave again to make the pressure of hydrogen 20 kg/cm$^2$ and, after stirring for about 30 seconds, the pressure of hydrogen was released. After repeating this operation once more, the pressure of hydrogen was increased to 50 kg/cm$^2$ and the temperature was increased to 140° C. in 30 minutes under stirring. The reaction was conducted at 140° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm$^2$ during the reaction. After finishing the reaction, the reaction mixture was cooled to the room temperature and the pressure was decreased to the atmospheric pressure. The reaction product was filtered with filter paper. The reaction product was then transferred to a washing vessel and washed with 100 ml of a 5 weight % aqueous solution of sodium hydroxide 3 times and then with 150 ml of distilled water 5 times. Hexane, water and the like were removed under the reduced pressure by using a rotary evaporator. The yield was 97 g. NMR and IR of the product were measured and it was confirmed that one of the end structures of the polymer was a mixture of (A) and (E) and the other was a mixture of (C), (F) and (D), in which (C) and (F) were the major structures and (D) was the minor structure.

Example of Preparation 12

Into a 500 ml glass flask equipped with a dropping funnel, a cooler and a stirrer, 80 g of toluene, 40 g of propionaldehyde diethyl acetal and 0.4 g of boron trifluoride diethyl etherate were charged. Into a dropping funnel, 116 g of 1-ethoxy-1-propene was charged and dropped in 60 minutes. The temperature of the reaction solution increased by the heat of reaction and the temperature was kept at about 30° C. by cooling with an ice water bath. After finishing the dropping, the solution was further stirred for 40 minutes. The reaction mixture was transferred to a washing vessel and washed with 150 ml of a 5 weight % aqueous solution of sodium hydroxide 3 times and then with 200 ml of water 3 times. The solvent and unreacted materials were removed under the reduced pressure by using a rotary evaporator to obtain 140 g of the crude product. The crude product had the kinematic viscosity of 34.4 cSt at 40° C.

Into a 1 liter autoclave made of SUS-316L, 120 g of the crude product, 300 g of hexane, 6 g of Raney nickel and 6 g of zeolite were charged. Hydrogen was introduced into the autoclave and the pressure of hydrogen was adjusted to 20 kg/cm$^2$. After stirring for about 30 seconds, the pressure was released. Hydrogen was introduced into the autoclave again to make the pressure of hydrogen 20 kg/cm$^2$ and, after stirring for about 30 seconds, the pressure of hydrogen was released. After repeating this operation once more, the pressure of hydrogen was increased to 50 kg/cm$^2$ and the temperature was increased to 130° C. in 30 minutes under stirring. The reaction was conducted at 130° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm$^2$ during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 50 ml of hexane twice. The washing liquid was combined with the reaction liquid and filtered with filter paper. The combined liquid was then transferred to a 1 liter washing vessel and washed with 150 ml of a 5 weight % aqueous solution of sodium hydroxide 3 times and then with 200 ml of distilled water 5 times. Hexane, water and the like were removed under the reduced pressure by using a rotary evaporator. The yield was 95 g. NMR and IR of the product were measured and it was confirmed that one of the end structures of the polymer was (J) and the other was a mixture of (K) and (L), in which (K) was the major structure and (L) was the minor structure.

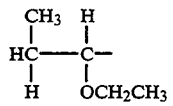
(J)

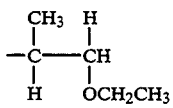
(K)

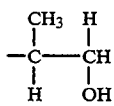
(L)

Example of Preparation 13

Into a 5 liter glass flask equipped with a dropping funnel, a cooler and a stirrer, 1000 g of toluene, 304 g of ethanol and 7.8 g of boron trifluoride diethyl etherate were charged. Into a dropping funnel, 3284 g of ethyl vinyl ether was charged and dropped in 4 hours and 30 minutes. During this period, the temperature of the reaction solution increased by the heat of reaction and the temperature was kept at about 25° C. by cooling with an ice water bath. After finishing the dropping, the solution was further stirred for 5 minutes. The reaction mixture was transferred to a washing vessel and washed with 1100 ml of a 5 weight % aqueous solution of sodium hydroxide 3 times and then with 1100 ml of water 3 times. The solvent and unreacted materials were removed under the reduced pressure by using a rotary evaporator to obtain 3397 g of the crude product.

Into a 2 liter autoclave made of SUS-316L, 600 g of the crude product, 600 g of hexane, 18 g of Raney nickel and 18 g of zeolite were charged. Hydrogen was introduced into the autoclave and the pressure of hydrogen was adjusted to 20 kg/cm$^2$. After stirring for about 30 seconds, the pressure was released. Hydrogen was introduced into the autoclave again to make the pressure of hydrogen 20 kg/cm$^2$ and, after stirring for about 30 seconds, the pressure of hydrogen was released. After repeating this operation once more, the pressure of hydrogen was increased to 50 kg/cm$^2$ and the temperature was increased to 140° C. in 30 minutes under stirring. The reaction was conducted at 140° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm$^2$ during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 100 ml of hexane twice. The washing liquid was combined with the reaction liquid and filtered with filter paper. The combined liquid was then transferred to a washing vessel and washed with 500 ml of a 5 weight % aqueous solution of sodium hydroxide 3 times and then with 500 ml of distilled water 5 times. Hexane, water and the like were removed under the reduced pressure by using a rotary evaporator. The yield was 492 g.

NMR and IR of the product were measured and it was confirmed that one of the end structures of the polymer was (A) and the other was a mixture of (C) and (D), in which (C) was the major structure and (D) was the minor structure.

Example of Preparation 14

Into a 5 liter glass flask equipped with a dropping funnel, a cooler and a stirrer, 1000 g of toluene, 500 g of acetaldehyde diethyl acetal and 5.0 g of boron trifluoride diethyl etherate were charged. Into a dropping funnel, 2700 g of ethyl vinyl ether was charged and dropped in 3 hours. The temperature of the reaction solution increased by the heat of reaction and the temperature was kept at about 25° C. by cooling with an ice water bath. After finishing the dropping, the solution was further stirred for 5 minutes. The reaction mixture was transferred to a washing vessel and washed with 1000 ml of a 5 weight % aqueous solution of sodium hydroxide 3 times and then with 1000 ml of water 3 times. The solvent and unreacted materials were removed under the reduced pressure by using a rotary evaporator to obtain 3040 g of the crude product. The crude product had the kinematic viscosity of 42.1 cSt at 40° C.

Into a 2 liter autoclave made of SUS-316L, 600 g of the crude product, 600 g of hexane, 18 g of Raney nickel and 18 g of zeolite were charged. Hydrogen was introduced into the autoclave and the pressure of hydrogen was adjusted to 20 kg/cm$^2$. After stirring for about 30 seconds, the pressure was released. Hydrogen was introduced into the autoclave again to make the pressure of hydrogen 20 kg/cm$^2$ and, after stirring for about 30 seconds, the pressure of hydrogen was released. After repeating this operation once more, the pressure of hydrogen was increased to 50 kg/cm$^2$ and the temperature was increased to 140° C. in 30 minutes under stirring. The reaction was conducted at 140° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm$^2$ during the reaction.

After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 100 ml of hexane twice. The washing liquid was combined with the reaction liquid and filtered with filter paper. The combined liquid was then transferred to a washing vessel and washed with 500 ml of a 5 weight % aqueous solution of sodium hydroxide 3 times and then with 500 ml of distilled water 5 times. Hexane, water and the like were removed under the reduced pressure by using a rotary evaporator. The yield was 495 g. The polymer had the same end structures as those in Example of Preparation 4.

Example of Preparation 15

Into a 5 liter glass flask equipped with a dropping funnel, a cooler and a stirrer, 1000 g of toluene, 450 g of acetaldehyde diethyl acetal and 4.5 g of boron trifluoride diethyl etherate were charged. Into a dropping funnel, 3200 g of ethyl vinyl ether was charged and dropped in 4 hours and 10 minutes. The temperature of the reaction solution increased by the heat of reaction and the temperature was kept at about 25° C. by cooling with an ice water bath. After finishing the dropping, the solution was further stirred for 5 minutes. The reaction mixture was transferred to a washing vessel and washed with 1000 ml of a 5 weight % aqueous solution of sodium hydroxide 3 times and then with 1000 ml of water 3 times. The solvent and unreacted materials were removed under the reduced pressure by using a rotary evaporator to obtain 3466 g of the crude product. The crude product had the kinematic viscosity of 76.1 cSt at 40° C.

Into a 2 liter autoclave made of SUS-316L, 600 g of the crude product, 600 g of hexane, 18 g of Raney nickel and 18 g of zeolite were charged. Hydrogen was introduced into the autoclave and the pressure of hydrogen was adjusted to 20 kg/cm$^2$. After stirring for about 30 seconds, the pressure was released. Hydrogen was introduced into the autoclave again to make the pressure of hydrogen 20 kg/cm$^2$ and, after stirring for about 30 seconds, the pressure of hydrogen was released. After repeating this operation once more, the pressure of hydrogen was increased to 50 kg/cm$^2$ and the temperature was increased to 140° C. in 30 minutes under stirring. The reaction was conducted at 140° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm$^2$ during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 100 ml of hexane twice. The washing liquid was combined with the reaction liquid and filtered with filter paper. The combined liquid was then transferred to a washing vessel and washed with 500 ml of a 5 weight % aqueous solution of sodium hydroxide 3 times and then with 500 ml of distilled water 5 times. Hexane, water and the like were removed under the reduced pressure by using a rotary evaporator. The yield was 498 g. The polymer had the same end structures as those in Example of Preparation 4.

Example of Preparation 16 (Comparative Example of Preparation)

Into a 5 liter glass flask equipped with a Dean and Stark tube, a cooler and a stirrer, 1091 g of pentaerythritol and 3909 g of n-hexanoic acid were charged and the mixture was heated under stirring. When the temperature of the solution reached 200° C., the temperature was kept constant for 3 hours. Then, the temperature was increased to 220° C. and kept at this temperature for 10 hours. During this period, the reaction started and water was formed. After the reaction was finished, the reaction solution was cooled to 150° C. and the major part of the unreacted hexanoic acid was recovered under the reduced pressure. The remaining solution was transferred to a washing vessel and, after being dissolved in 2 liter of hexane, washed with 1500 ml of a 3 weight % aqueous solution of sodium hydroxide 3 times and with 1500 ml of water 3 times. Further, 800 g of an ion exchange resin was added and the mixture was stirred for 3 hours. The ion exchange resin was removed by filtration and hexane was removed under the reduced pressure by using a rotary evaporator. The yield of the lubricant of polyolester was 3390 g.

Example 1

By using the lubricating oil of the present invention prepared in Example of Preparation 1, kinematic viscosity, compatibility with Flon 134a, volume specific resistance and stability to hydrolysis were measured. The results obtained are shown in Table 1.

Conditions of the measurements were as following.

(1) Kinematic viscosity

Kinematic viscosity was measured according to the method of Japanese Industrial Standard K-2283 (1983) by using a glass capillary viscometer.

(2) Compatibility (a) Flon 134a

A sample of a specified amount adjusted to make 5 weight % or 10 weight % based on Flon 134a (1,1,1,2-tetrafluoroethane) was charged into a pressure resistant glass ampoule and the ampoule was connected to the vacuum line and the line for Flon 134a gas. The ampoule was degassed in vacuum at the room temperature, cooled with liquid nitrogen and a specified amount of Flon 134a was taken into the ampoule. The ampoule was then sealed and the temperature at which the phase separation starts was measured by slowly cooling the sample from the room temperature to −60° C. in a thermostatted vessel for the measurement of the compatibility at the lower temperature side and by slowly heating the sample from the room temperature to +80° C. in a thermostatted vessel for the measurement of the compatibility at the higher temperature side. A lower temperature of the phase separation is preferable in the measurement at the lower temperature side and a higher temperature of the phase separation is preferable in the measurement at the higher temperature side.

(b) Flon 32

A sample of a specified amount adjusted to make 10 weight % or 20 weight % based on Flon 32 (difluoromethane) was charged into a pressure resistant glass ampoule and the ampoule was connected to the vacuum line and the line for Flon 32 gas. The ampoule was degassed in vacuum at the room temperature, cooled with liquid nitrogen and a specified amount of Flon 32 was taken into the ampoule. The ampoule was then sealed and the temperature at which the phase separation starts was measured by slowly cooling the sample from the room temperature in a thermostatted vessel for the measurement of the compatibility at the lower temperature side and by slowly heating the sample from the room temperature to +40° C. in a thermostatted vessel for the measurement of the compatibility at the higher temperature side. A lower temperature of the phase separation is preferable in the measurement at the lower temperature side and a higher temperature of the phase separation is preferable in the measurement at the higher temperature side.

(3) Volume specific resistance

A sample was dried under the reduced pressure (0.3 to 0.8 mmHg) at 100° C. for 1 hour and then charged into a liquid cell for the measurement of volume specific resistance which is placed into a thermostatted vessel at 80° C. After the sample was kept in the thermostatted vessel at 80° C. for 40 minutes, the volume specific resistance was measured at the added electric pressure of 250 V by using an ultrainsulation meter R8340 produced by Advantest Co.

(4) Stability to hydrolysis

Into a bottle of pressure resistant glass of 250 ml capacity, 75 g of a sample, 25 g of water and a piece of copper (13×50 mm) were placed and the atmosphere in the bottle was replaced with nitrogen. The sample was kept in a rotatory thermostatted vessel at the temperature of 102° C. for 192 hours. After finishing the test, appearance of the sample and condition of the piece of copper were visually observed and the total acid value was measured.

Example 2 to 15

By using the lubricating oils of the present invention prepared in Examples of Preparation 2 to 15, kinematic viscosity, compatibility with Flon 134a, volume specific resistance and stability to hydrolysis were measured by the same methods as in Example 1. The results obtained are shown in Table 1.

Compatibility with Flon 32 was also measured with the lubricating oils prepared in Examples of Preparation 14 and 15. The results are shown in Table 2.

Comparative Example 1

Kinematic viscosity, compatibility with Flon 134a, volume specific resistance and stability to hydrolysis were measured by using a commercial paraffinic mineral oil (VG32) by the same methods as in Example 1. The results obtained are shown in Table 1.

Comparative Example 2

Kinematic viscosity, compatibility with Flon 134a, volume specific resistance and stability to hydrolysis were measured by using polypropylene glycol Unilub MB11 (a product of Nippon Yushi Co., Ltd.) by the same methods as in Example 1. The results obtained are shown in Table 1.

Comparative Example 3

Kinematic viscosity, compatibility with Flon 134a, volume specific resistance and stability to hydrolysis were measured by using the lubricating oil of polyolester prepared in Example of Preparation 16 by the same methods as in Example 1. The results obtained are shown in Table 1.

TABLE 1

| | | kinematic viscosity (cSt) | | compatibility with Flon 134a | | | |
| | | | | temperature of separation at low temperature (°C.) | | temperature of separation at high temperature (°C.) | |
| | sample*1) | 40° C. | 100° C. | 5% | 10% | 5% | 10% |
| --- | --- | --- | --- | --- | --- | --- | --- |
| Example 1 | Ex. Prpn. 1 | 17.8 | 3.68 | −60.0> | −60.0> | 80.0< | 80.0< |
| Example 2 | Ex. Prpn. 2 | 49.8 | 6.55 | −60.0> | −60.0> | 80.0< | 80.0< |
| Example 3 | Ex. Prpn. 3 | 51.0 | 6.57 | −60.0> | −60.0> | 80.0< | 80.0< |
| Example 4 | Ex. Prpn. 4 | 41.2 | 6.24 | −60.0> | −60.0> | 80.0< | 80.0< |
| Example 5 | Ex. Prpn. 5 | 37.9 | 6.07 | −60.0> | −60.0> | 80.0< | 80.0< |
| Example 6 | Ex. Prpn. 6 | 22.8 | 3.77 | −60.0> | −60.0> | 80.0< | 80.0< |
| Example 7 | Ex. Prpn. 7 | 631.0 | 26.30 | −60.0> | −60.0> | 80.0< | 80.0< |
| Example 8 | Ex. Prpn. 8 | 38.1 | 5.18 | −60.0> | −60.0> | 80.0< | 80.0< |
| Example 9 | Ex. Prpn. 9 | 37.9 | 5.67 | −60.0> | −60.0> | 80.0< | 80.0< |
| Example 10 | Ex. Prpn. 10 | 48.8 | 6.05 | −60.0> | −60.0> | 80.0< | 80.0< |
| Example 11 | Ex. Prpn. 11 | 40.0 | 5.85 | −60.0> | −60.0> | 80.0< | 80.0< |
| Example 12 | Ex. Prpn. 12 | 26.8 | 4.20 | −60.0> | −60.0> | 80.0< | 80.0< |
| Example 13 | Ex. Prpn. 13 | 16.5 | 3.41 | −60.0> | −60.0> | 80.0< | 80.0< |
| Example 14 | Ex. Prpn. 14 | 31.6 | 5.15 | −60.0> | −60.0> | 80.0< | 80.0< |
| Example 15 | Ex. Prpn. 15 | 55.2 | 7.32 | −60.0> | −60.0> | 80.0< | 80.0< |
| Comparative Example 1 | mineral oil*2) | 37.7 | 4.6 | not dissolved | | not dissolved | |
| Comparative Example 2 | glycol*3) | 56.1 | 10.8 | −60.0> | −60.0> | 55.5 | 51.5 |
| Comparative Example 3 | Ex. Prpn. 16 | 17.9 | 4.0 | −60.0> | −45.0 | 80.0< | 80.0< |

| | volume specific resistance at 80° C. ($\Omega \cdot$ cm) | after the hydrolysis test | | |
| | | sample oil | | appearance of piece of copper |
| | | appearance | total acid value (mg KOH/g) | |
| --- | --- | --- | --- | --- |
| Example 1 | $1.5 \times 10^{12}$ | good | 0.5> | good |
| Example 2 | $3.9 \times 10^{12}$ | good | 0.5> | good |
| Example 3 | $1.5 \times 10^{12}$ | good | 0.5> | good |
| Example 4 | $2.0 \times 10^{13}$ | good | 0.5> | good |
| Example 5 | $1.6 \times 10^{13}$ | good | 0.5> | good |
| Example 6 | $6.1 \times 10^{12}$ | good | 0.5> | good |
| Example 7 | $1.3 \times 10^{12}$ | good | 0.5> | good |

TABLE 1-continued

| | | | | |
|---|---|---|---|---|
| Example 8 | $1.5 \times 10^{12}$ | — | — | — |
| Example 9 | $1.9 \times 10^{12}$ | good | 0.5> | good |
| Example 10 | $1.4 \times 10^{12}$ | — | — | — |
| Example 11 | $1.9 \times 10^{13}$ | good | 0.5> | good |
| Example 12 | $6.5 \times 10^{13}$ | good | 0.5> | good |
| Example 13 | $2.3 \times 10^{13}$ | good | 0.5> | good |
| Example 14 | $1.5 \times 10^{14}$ | good | 0.5> | good |
| Example 15 | $5.8 \times 10^{13}$ | good | 0.5> | good |
| Comparative Example 1 | $2.0 \times 10^{14}$ | good | 0.5> | good |
| Comparative Example 2 | $5.8 \times 10^{8}$ | good | 0.5> | good |
| Comparative Example 3 | $4.0 \times 10^{12}$ | poor | 2.5 | poor |

*1)Ex. Prpn.: Example of Preparation
*2)a commercial paraffinic mineral oil
*3)polypropylene glycol

TABLE 2

| | compatibility with Flon 32 | | | |
|---|---|---|---|---|
| | temperature of separation at low temperature (°C.) Flon/sample (wt. %) | | temperature of separation at high temperature (°C.) Flon/sample (wt. %) | |
| | 90/10 | 80/20 | 90/10 | 80/20 |
| Example 14 | −20 | −15 | 40< | 40< |
| Example 15 | −5 | 0 | 40< | 40< |

What is claimed is:

1. A lubricating oil composition for compression-type refrigerators which comprises a refrigerant and a lubricant, said lubricant comprising as the main component thereof a polyvinyl ether compound having the constituting unit expressed by the general formula (I):

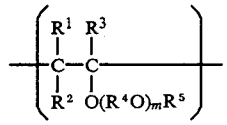

(I)

wherein $R^1$, $R^2$ and $R^3$ are a hydrogen atom or a hydrocarbon group having 1 to 8 carbon atoms, respectively, and may be the same or different from each other, $R^4$ is a bivalent hydrocarbon group having 2 to 10 carbon atoms, $R^5$ is a hydrocarbon group having 1 to 10 carbon atoms, m is a number the average of which is in the range of 0 to 10, $R^1$ to $R^5$ may the same or different between the constituting units and a plurality of $R^4O$'s may be the same or different from each other when a plurality of $R^4O$'s are present, the number of units represented by the formula (I) being sufficient to provide a kinematic viscosity in the range of 5 to 1000 cSt at 40° C.

2. A lubricating oil composition as claimed in claim 1, wherein the polyvinyl ether compound has a structure in which one end is expressed by the general formula (II):

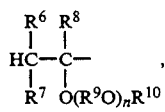

(II)

wherein $R^6$, $R^7$ and $R^8$ are a hydrogen atom or a hydrocarbon group having 1 to 8 carbon atoms, respectively, and may be the same or different from each other, $R^9$ is a bivalent hydrocarbon group having 2 to 10 carbon atoms, $R^{10}$ is a hydrocarbon group having 1 to 10 carbon atoms, n is a number the average of which is in the range of 0 to 10 and a plurality of $R^9O$'s may be the same or different from each other when a plurality of $R^9O$'s are present.

3. A lubricating oil composition as claimed in claim 1, wherein the polyvinyl ether compound has a structure in which one end is expressed by the general formula (II):

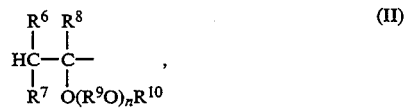

(II)

wherein $R^6$, $R^7$ and $R^8$ are a hydrogen atom or a hydrocarbon group having 1 to 8 carbon atoms, respectively, and may be the same or different from each other, $R^9$ is a bivalent hydrocarbon group having 2 to 10 carbon atoms, $R^{10}$ is a hydrocarbon group having 1 to 10 carbon atoms, n is a number the average of which is in the range of 0 to 10 and a plural of $R^9O$'s may be the same or different from each other when a plural of $R^9O$'s are present, and the other end is expressed by (III):

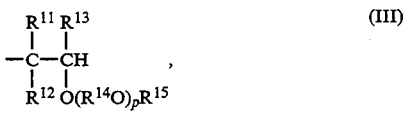

(III)

wherein $R^{11}$, $R^{12}$ and $R^{13}$ are a hydrogen atom or a hydrocarbon group having 1 to 8 carbon atoms, respectively, and may be the same or different from each other, $R^{14}$ is a bivalent hydrocarbon group having 2 to 10 carbon atoms, $R^{15}$ is a hydrocarbon group having 1 to 10 carbon atoms, p is a number the average of which is in the range of 0 to 10 and a plural of $R^{14}O$'s may be the same or different from each other when a plural of $R^{14}O$'s are present.

4. A lubricating oil composition as claimed in claim 2, wherein the polyvinyl ether compound has a structure in which one end is expressed by the general formula (II) and the other end is expressed by the general formula (IV):

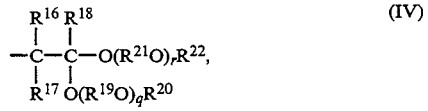

(IV)

wherein $R^{16}$, $R^{17}$ and $R^{18}$ are a hydrogen atom or a hydrocarbon group having 1 to 8 carbon atoms, respectively, and may be the same or different from each other, $R^{19}$ and $R^{21}$ are a bivalent hydrocarbon group having 2 to 10 carbon atoms, respectively, and may be the same or different from each other, $R^{20}$ and $R^{22}$ are a hydrocarbon group having 1 to 10 carbon atoms, respectively, and may be the same or different from each other, q and r are a number the average of which is in the range of 0 to 10, respectively, and may be the same or different from each other, a plural of $R^{19}O$'s may be the same or different from each other when a plural of $R^{19}O$'s are present and a plural of $R^{21}O$'s may be the same or different from each other when a plural of $R^{21}O$'s are present.

5. A lubricating oil composition as claimed in claim 2, wherein the polyvinyl ether compound has a structure in which one end is expressed by the general formula (II) and the other end comprises an olefinic unsaturated bond.

6. A lubricating oil composition as claimed in claim 2, wherein the polyvinyl ether compound has the structure in which one end is expressed by the general formula (II) and the other end is expressed by the general formula (V):

wherein $R^{23}$, $R^{24}$ and $R^{25}$ are a hydrogen atom or a hydrocarbon group having 1 to 8 carbon atoms, respectively and may be the same or different from each other.

7. A lubricating oil composition as claimed in claim 1, wherein the polyvinyl ether compound is a mixture of two or more of the compounds selected from the group consisting of a compound having the structure in which one end is expressed by the general formula (II):

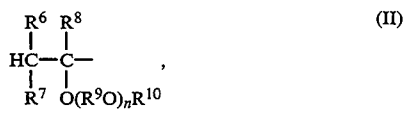

wherein $R^6$, $R^7$ and $R^8$ are a hydrogen atom or a hydrocarbon group having 1 to 8 carbon atoms, respectively, and may be the same or different from each other, $R^9$ is a bivalent hydrocarbon group having 2 to 10 carbon atoms, $R^{10}$ is a hydrocarbon group having 1 to 10 carbon atoms, n is a number the average of which is in the range of 0 to 10 and a plurality of $R^9O$'s may be the same or different from each other when a plurality of $R^9O$'s are present and the other end is expressed by the general formula (III):

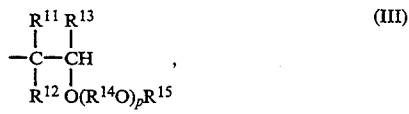

wherein $R^{11}$, $R^{12}$ and $R^{13}$ are a hydrogen atom or a hydrocarbon group having 1 to 8 carbon atoms, respectively, and may be the same or different from each other, $R^{14}$ is a hydrocarbon group having 2 to 10 carbon atoms, $R^{15}$ is a hydrocarbon group having 1 to 10 carbon atoms, p is a number the average of which is in the range of 0 to 10 and a plurality of $R^{14}O$'s may be the same or different from each other when a plurality of $R^{14}O$'s are present, a compound having the structure in which one end is expressed by the general formula (II) and the other end is expressed by the general formula (IV):

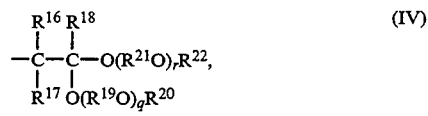

wherein $R^{16}$, $R^{17}$ and $R^{18}$ are a hydrogen atom or a hydrocarbon group having 1 to 8 carbon atoms, respectively, and may be the same or different from each other, $R^{19}$ and $R^{21}$ are a bivalent hydrocarbon group having 2 to 10 carbon atoms, respectively, and may be the same or different from each other, $R^{20}$ and $R^{22}$ are a hydrocarbon group having 1 to 10 carbon atoms, respectively, and may be the same or different from each other, q and r are a number the average of which is in the range of 0 to 10, respectively, and may be the same or different from each other, a plurality of $R^{19}O$'s may be the same or different from each other when a plurality of $R^{19}O$'s are present and a plurality of $R^{21}O$'s may be the same or different from each other when a a plurality of $R^{21}O$'s are present, a compound having the structure in which one end is expressed by the general formula (II) and the other end comprises an olefinic unsaturated bond and a compound having the structure in which one end is expressed by the general formula (II) and the other end is expressed by the general formula (V):

wherein $R^{23}$, $R^{24}$ and $R^{25}$ are a hydrogen atom or a hydrocarbon group having 1 to 8 carbon atoms, respectively, and may be the same or different from each other.

8. A lubricating oil composition as claimed in claim 1, wherein the polyvinyl ether compound is a mixture of a compound having the structure in which one end is expressed by the general formula (II):

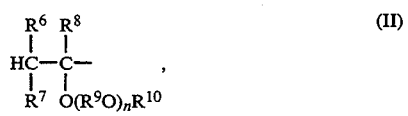

wherein $R^6$, $R^7$ and $R^8$ are a hydrogen atom or a hydrocarbon group having 1 to 8 carbon atoms, respectively, and may be the same or different from each other, $R^9$ is a bivalent hydrocarbon group having 2 to 10 carbon atoms, $R^{10}$ is a hydrocarbon group having 1 to 10 carbon atoms, n is a number the average of which is in the range of 0 to 10 and a plurality of $R^9O$'s may be the same or different from each other when a plurality of $R^9O$'s are present and the other end is expressed by the general formula (III):

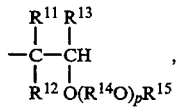
(III)

wherein $R^{11}$, $R^{12}$ and $R^{13}$ are a hydrogen atom or a hydrocarbon group having 1 to 8 carbon atoms, respectively, and may be the same or different from each other, $R^{14}$ is a bivalent hydrocarbon group having 2 to 10 carbon atoms, $R^{15}$ is a hydrocarbon group having 1 to 10 carbon atoms, p is a number the average of which is in the range of 0 to 10 and a plurality of $R^{14}O$'s may be the same or different from each other when a plurality of $R^{14}O$'s are present and a compound having the structure in which one end is expressed by the general formula (II) and the other end is expressed by the general formula (V):

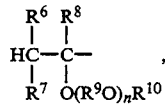
(V)

wherein $R^{23}$, $R^{24}$ and $R^{25}$ are a hydrogen atom or a hydrocarbon group having 1 to 8 carbon atoms, respectively, and may be the same or different from each other.

9. A lubricating oil composition as claimed in claim 1, wherein the polyvinyl ether compound is a mixture of a compound having the structure in which one end is expressed by the general formula (II):

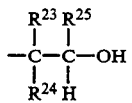
(II)

wherein $R^6$, $R^7$ and $R^8$ are a hydrogen atom or a hydrocarbon group having 1 to 8 carbon atoms, respectively, and may be the same or different from each other, $R^9$ is a bivalent hydrocarbon group having 2 to 10 carbon atoms, $R^{10}$ is a hydrocarbon group having 1 to 10 carbon atoms, n is a number the average of which is in the range of 0 to 10 and a plurality of $R^9O$'s may be the same or different from each other when a plurality of $R^9O$'s are present and the other end is expressed by the general formula (IV):

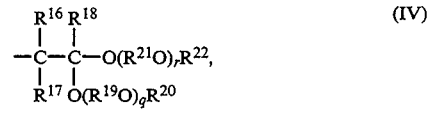
(IV)

wherein $R^{16}$, $R^{17}$ and $R^{18}$ are a hydrogen atom or a hydrocarbon group having 1 to 8 carbon atoms respectively, and may be the same or different from each other, $R^{19}$ and $R^{21}$ are a bivalent hydrocarbon group having 2 to 10 carbon atoms, respectively, and may be the same or different from each other, $R^{20}$ and $R^{22}$ are a hydrocarbon group having 1 to 10 carbon atoms, respectively, and may be the same or different from each other, q and r are a number the average of which is in the range of 0 to 10, respectively, and may be the same or different from each other, a plurality of $R^{19}O$'s may be the same or different from earth other when a plurality of $R^{19}O$'s are present and a plurality of $R^{21}O$'s may be the same or different from each other when a plurality of $R^{21}O$'s are present, and a compound having the structure in which one end is expressed by the general formula (II) and the other end comprises an olefinic unsaturated bond.

10. A lubricating oil composition as claimed in any one of claims 1 to 9 or 2, wherein the kinematic viscosity at 40° C. is in the range of 5 to 800 cSt.

11. A lubricating oil composition as claimed in claim 1, wherein the composition comprises a hydrofluorocarbon as the refrigerant.

12. A lubricating oil composition as claimed in claim 1, wherein the composition comprises a hydrochlorofluorocarbon as the refrigerant.

13. A lubricating oil composition as claimed in claim 1, wherein the composition comprises 1,1,1,2-tetrafluoroethane as the refrigerant.

14. A lubricating oil composition as claimed in claim 1, wherein the composition comprises a difluoromethane as the refrigerant.

* * * * *